(12) United States Patent
Brunel

(10) Patent No.: US 6,575,939 B1
(45) Date of Patent: Jun. 10, 2003

(54) DEVICE FOR AUTOMATIC INJECTION OF A DOSE OF MEDICINAL PRODUCT

(75) Inventor: Marc Brunel, Toulouse (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/601,473

(22) PCT Filed: Dec. 21, 1998

(86) PCT No.: PCT/FR98/02809

§ 371 (c)(1),
(2), (4) Date: Aug. 3, 2000

(87) PCT Pub. No.: WO99/39759

PCT Pub. Date: Aug. 12, 1999

(30) Foreign Application Priority Data

Feb. 4, 1998 (FR) .............................................. 98 01298

(51) Int. Cl.⁷ ................................................. A61M 5/00
(52) U.S. Cl. ........................ 604/187; 604/110; 604/194; 604/195; 604/208
(58) Field of Search ................................ 604/187, 194, 604/195, 196, 197, 198, 199, 208, 209, 210, 211, 218, 235; 222/340

(56) References Cited

U.S. PATENT DOCUMENTS

| 3,712,301 A | 1/1973 | Sarnoff | |
|---|---|---|---|
| 3,797,489 A | 3/1974 | Sarnoff | |
| 5,364,362 A | * 11/1994 | Schulz | 604/115 |
| 5,709,662 A | * 1/1998 | Olive et al. | 604/110 |
| 5,957,897 A | * 9/1999 | Jeffrey | 604/110 |
| 6,210,369 B1 | * 4/2001 | Wilmot et al. | 604/157 |

FOREIGN PATENT DOCUMENTS

| EP | 0 516 473 | 12/1992 |
|---|---|---|
| EP | 0 518 416 | 12/1992 |
| EP | 0 577 448 | 1/1994 |
| FR | 2 654 938 | 5/1991 |
| WO | WO 94/21316 | 9/1994 |
| WO | WO 95/35126 | 12/1995 |

* cited by examiner

Primary Examiner—David A. Scherbel
Assistant Examiner—John K Fristoe
(74) Attorney, Agent, or Firm—William H. Holt

(57) ABSTRACT

The invention concerns a single-use device for injecting a dose of a medicinal product, comprising a syringe (1) and a piston rod (7) provided with a collar (9) housed in a casing formed of two parts, a front part (11) and a rear part (10), fitted inside each other and capable of sliding in relation to each other over a short traverse between two positions, a retracted position and a forward position. This device additionally includes means (35) for supporting the collar (9) of the piston rod (7) arranged so as to permit, on the one hand, injection under the effect of a propulsion spring (50) in the forward position of the parts (10, 11) of the casing and, on the other hand, backward movement of the syringe (1) inside the casing, after injection, in the retracted position of the said parts of the casing. It also includes means (28, 29) for viewing the supporting means (35) at the end of injection.

12 Claims, 8 Drawing Sheets

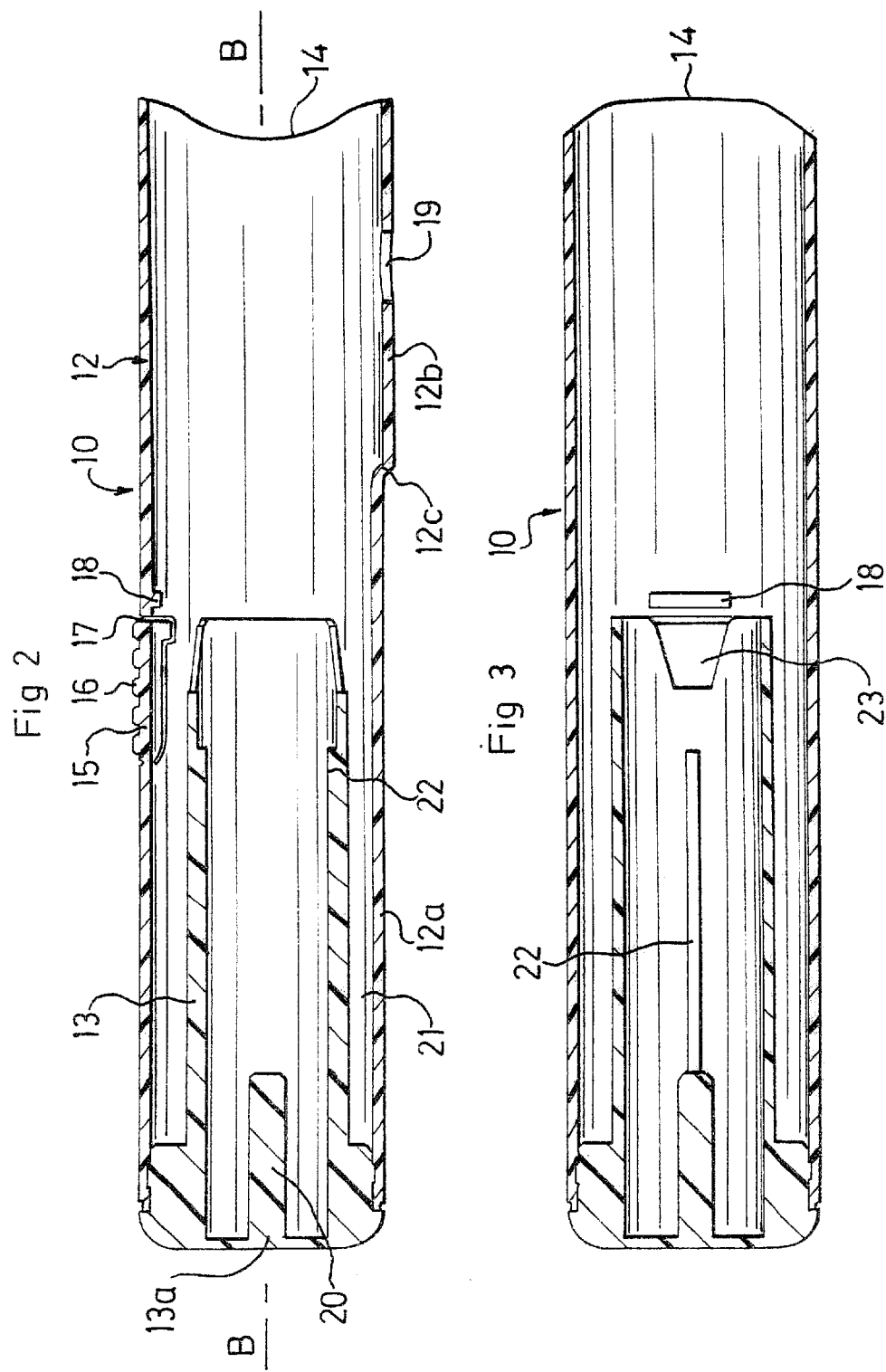

Figure 1:
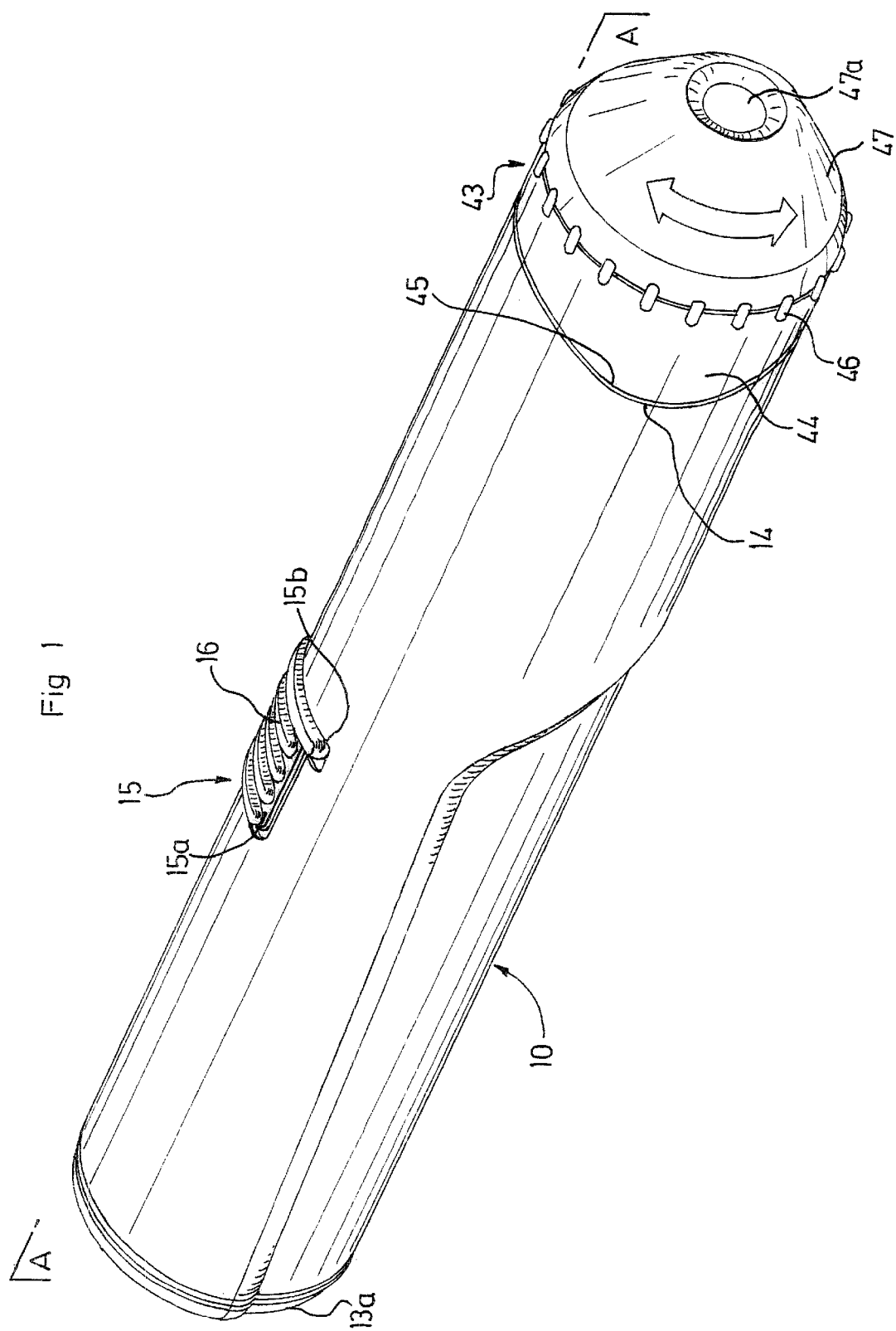

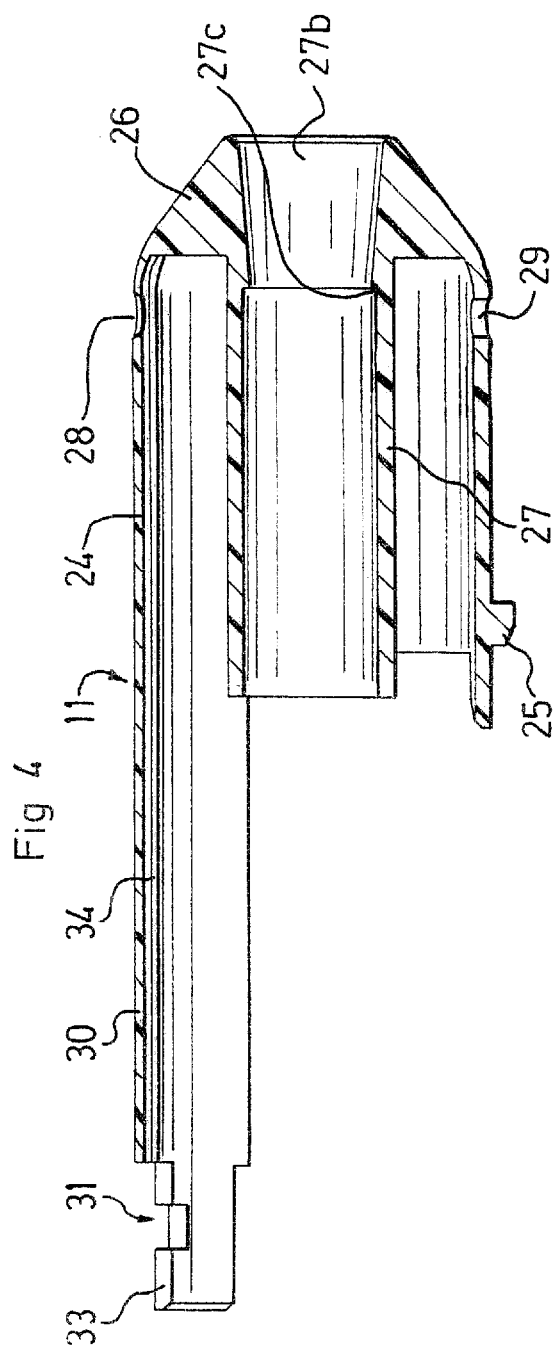
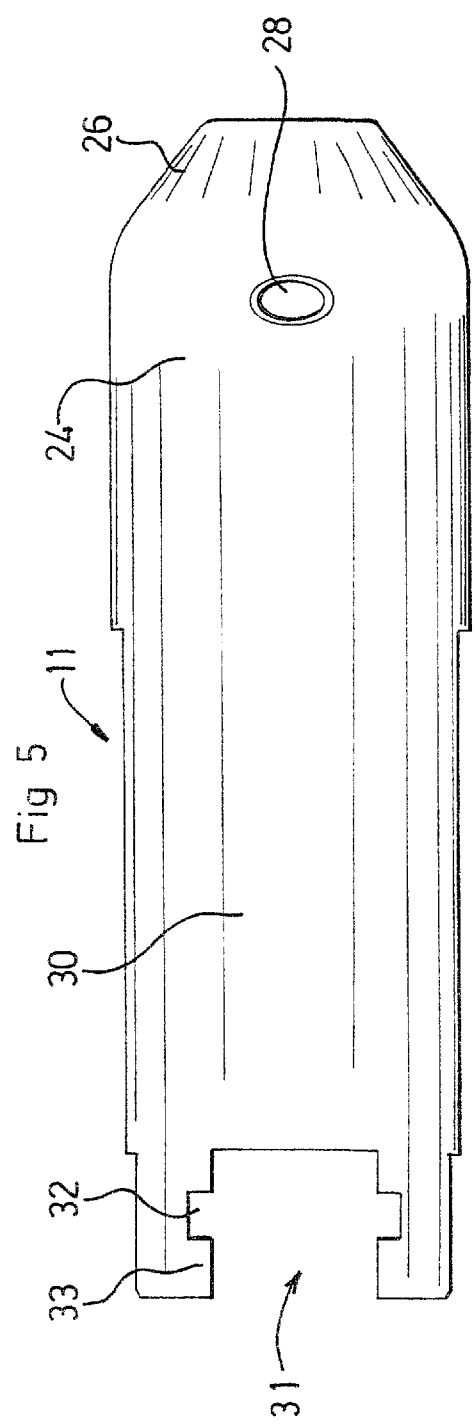

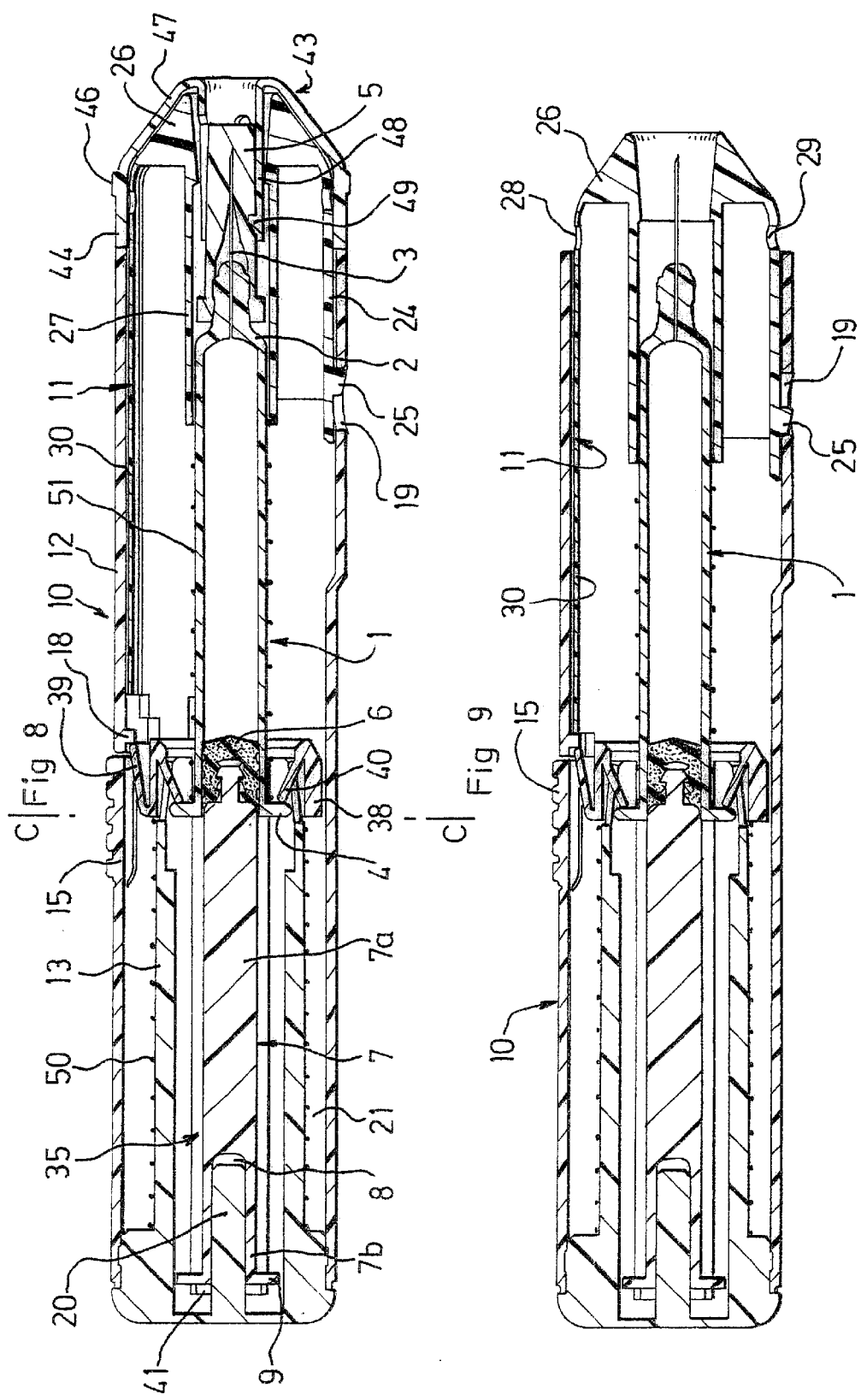

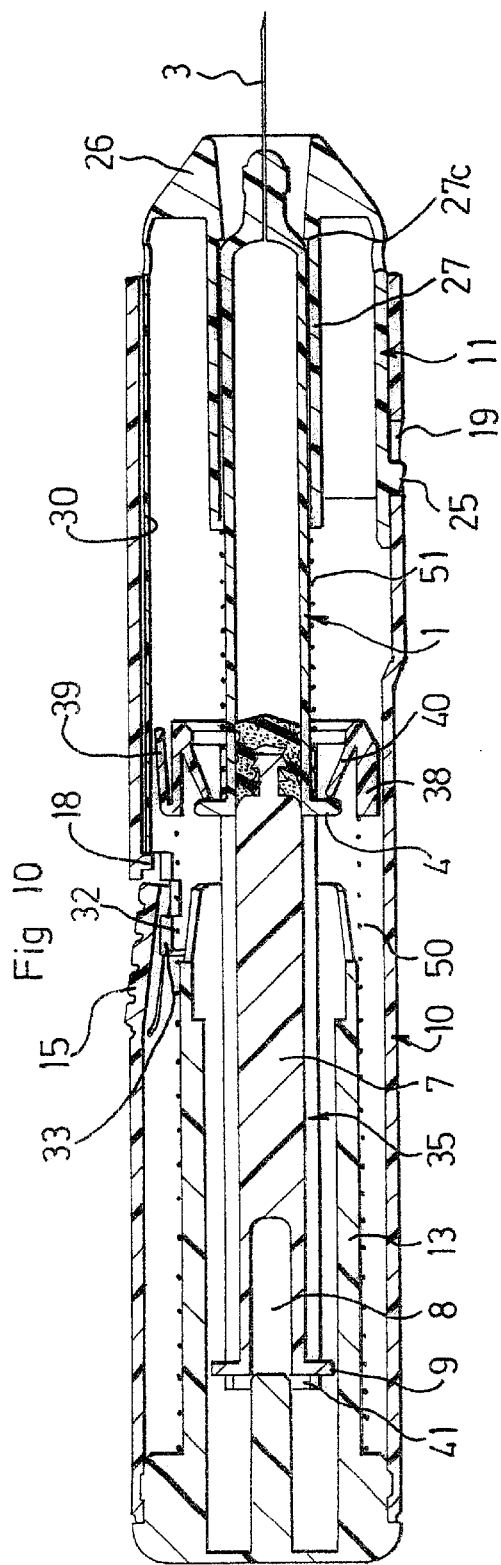

DEVICE FOR AUTOMATIC INJECTION OF A DOSE OF MEDICINAL PRODUCT

The invention concerns a device for automatically injecting a dose of a medicinal product.

A number of injection devices exist at the present time enabling an inexperienced patient to self-administer a dose of a medicinal product without having to force the needle into himself or herself and actuate the piston of the syringe.

Such injection devices are in particular described in patents EP 516,473, U.S. Pat. No. 3,797,489, U.S. Pat. No. 3,712,301, WO 95/35126, FR 2,654,938, and EP 577 448.

At the present time, for obvious safety reasons, the tendency consists of producing injection devices such as that described in patent EP 516 473, for single use including a propulsion spring designed to inject the medicinal product, and a propulsion spring designed to push the syringe back automatically into the casing after injection. According to this design, the needle of the syringe only projects from the casing during the time of injection and no risk of injury with a soiled needle is therefore to be feared.

Although such injection devices provide an appreciable advantage as regards their safety of use, they however have several disadvantages. In point of fact, in the first place, on account of the manufacturing dimensional tolerances of the syringes, and of the presence of the return propulsion spring, it is virtually impossible to guarantee injection of all the dose enclosed in the said syringes. Now, for certain products such as heparin or specific vaccines, the dose of the product injected must be guaranteed in a very precise manner, a condition which current injection devices cannot systematically fulfill.

Moreover, most of the current injection devices offering this safety of use for the patient prove to have a complexity which leads to a cost price which is hardly compatible with that of a single-use device. Moreover, on account of their design, they generally require the use of specific syringes of which the cost price is out of all proportion with that of conventional syringes used without an automatic injection device.

These last two disadvantages have been overcome by the injection device described in patent application WO 94/21316 which comprises:

- a long narrow casing having a front wall pierced by an orifice, and formed of two parts, a front part and a rear part, fitted one into the other and capable of sliding longitudinally in relation to each other over a short traverse so as to be able to undergo a relative movement between two positions: a retracted, so called rest position, of the rear part with respect to the front part obtained naturally in the absence of an external force exerted on the said parts, and a forward, so-called injection position, of the rear part with respect to the front part obtained by means of a longitudinal force exerted on the said rear part,
- a syringe disposed in the casing and including a syringe body housing a piston, provided with a finger rest ring and carrying a needle,
- a piston rod provided with a collar and extending into the rear extension of the syringe,
- means for supporting the collar of the piston rod,
- a propulsion spring extending between the means for supporting the collar of the piston rod and the bottom of the rear part of the casing,
- means for locking in translation the means for supporting the collar of the piston rod capable of supporting them inside the casing in a position where the propulsion spring is compressed, and where the syringe is entirely housed inside the said casing, and capable of allowing their movement towards a forward position at the end of injection, produced by the propulsion spring, after the parts of the casing are moved from their retracted position to their forward position,
- a device for stopping the syringe body in a forward position of the latter where the needle extends at least partially through the orifice of the casing,
- means for triggering the means for supporting the collar of the piston rod capable of freeing the said collar, in the forward position of the said supporting means, after the parts of the casing are moved from their forward position to their retracted position,
- and a return propulsion spring with a force less than that of the propulsion spring, disposed around the syringe body so as to be compressed by the finger rest ring of the said syringe body when the latter is moved to its forward position.

However, such an injection device does not enable the aforementioned first disadvantage to be overcome, namely to guarantee injection of the entire dose.

The present invention aims to overcome this disadvantage and its object is to provide an automatic injection device designed so as to enable a strictly defined dose of a medicinal product to be injected systematically.

Another object of the invention is to provide an injection device with a simplified design and therefore with a cost price compatible with that of a single-use device.

Another object of the invention is to provide an injection device which can be used with pre-filled syringes of the traditional type.

To this end, the invention concerns a device for automatically injecting a dose of a medicinal product of the type described in patent application WO 94/21316.

According to the invention, this injection device is characterized in that:

- it includes means for viewing provided in the wall of the casing so as to enable the means for supporting the collar of the piston rod in their forward position to be seen,
- means for supporting the collar of the piston rod comprising:
  - an inner, so called guide tube, extending into the rear part of the casing so as to delimit a peripheral annular space within the latter adapted so as to house the propulsion spring in the compressed position of the said spring,
  - a cage with a form adapted so as to slide inside the guide tube, and to house the piston rod and the collar thereof, the said cage including towards one of its ends, the so-called rear end, an internal device for locking the collar of the piston rod capable of deforming radially and, towards its other forward end, a front wall for stopping the propulsion spring and for contacting the means of locking in translation the said supporting means in the retracted position of the latter,
  - the said guide tube and cage being adapted so that, in the forward position of the supporting means, the device for locking the collar of the piston rod remains imprisoned in the guide tube in the forward relative position of the parts of the casing, and is freed in the retracted relative position of the said parts of the casing.

According to the invention, injection is carried out by applying first of all and in a conventional manner the forward end of the casing against the skin. A pressure exerted on the rear part of the casing then permits the triggering of the propulsion spring and therefore the injection of the product. At the end of this injection, the patient has a visual indication of the end of the traverse which informs him or her that the entire dose has been injected. He or she may then relax the pressure on the rear part of the casing, a relaxation which will enable is this rear part to retract and consequently allow the syringe to return into the casing under the action of the return propulsion spring.

Such an injection device which firstly includes a casing in two parts of which the relative movement enables the tolerances in variations in the lengths of the syringes to be absorbed and enables injection and subsequent return of the syringe inside the casing to be triggered, and secondly includes a visual indication of the end of injection, thus makes it possible to deliver systematically the entire product enclosed in the syringe and moreover constitutes a single-use device eliminating any risk of pricking before and after use.

In addition, absorption of the variation tolerances in the lengths of the syringes is obtained in a very simple manner by providing a sufficient margin concerning the length of the cage remaining imprisoned in the inner tube at the end of injection.

Moreover, the guide tube and the cage preferably have dimensions adapted so as to house the piston rod and the finger rest ring of the syringe body, the said cage including an internal device for stopping the finger rest ring of the syringe body in the retracted position of the said cage, and a front wall provided with an opening for permitting relative movement of this cage and the syringe body in the forward position of the latter.

The presence of this internal device for stopping the finger rest ring of the syringe body advantageously makes it possible to prevent the said syringe body from being entrained forwards when the protective end of the needle is withdrawn. Indeed, this entrainment, observed with current devices, and which tends to compress the return propulsion spring, results in difficulties for the user who, observing a resistance resulting from this compression, may hesitate to exert forces aimed at overcoming this resistance.

According to another characteristic of the invention, this injection device is adapted so as to be used with a traditional syringe of which the finger rest ring has a truncated annular form and includes two diametrically opposed flats. To this end, the cage consists of a stirrup having two longitudinal legs arranged so that each comes into contact with a flat of the finger rest ring.

Such a stirrup has the advantage of constituting an element for locking the syringe body in rotation, having a small overall transverse size, which combined with the arrangement of the propulsion spring in an annular space situated around the said stirrup, results in an injection device being obtained with a reduced overall size.

According to two preferred embodiments involving the stirrup:
  the internal device for locking the collar of the piston rod consists of transverse grooves provided facing the legs of the stirrup,
  this stirrup includes a ring in the rear extension of which the longitudinal legs extend, the internal device for stopping the finger rest ring of the syringe body including at least one inclined tongue extending longitudinally inside the said ring.

According to another characteristic of the invention:
  the rear part of the casing has the form externally of a sleeve with a generally cylindrical form,
  the front part of the casing has dimensions adapted so as to be housed over most of its length inside the rear part of the said casing,
  guiding devices are adapted so as to enable the rear part of the casing to move over a short traverse along the front part of the said casing.

This arrangement of the front and rear parts of the casing makes it possible to obtain a casing which is perfectly rigid in flexion and which is therefore very safe in operation by the user.

According to another characteristic of the invention, the means for locking in translation the means for supporting the collar of the piston rod comprise:
  a radially deformable stop device secured to the supporting means,
  an internal axial device for stopping the deformable stop device, provided inside the rear part of the casing,
  a trigger provided in the peripheral wall of the rear part of the casing so that it can deform and free the, device for stopping the supporting means, in the retracted position of the latter,
  and an opening provided in the peripheral wall of the front part of the casing and with a form adapted firstly so that the stop devices extend through the said opening and secondly so as to enable the trigger to be actuated only in the forward relative position of the said, parts of the casing.

This arrangement makes it possible to provide a guarantee against any accidental triggering of the injection since the latter requires, first of all, a pressure to be exerted on the casing, and then secondly, a pressure to be applied to the trigger so as to retract the deformable device for stopping the supporting means.

According to a preferred embodiment, the trigger has a longitudinal T-shape, the opening having a corresponding shape and being provided so as to have a transverse arm offset longitudinally from the transverse bar of the trigger in the retracted relative position of the parts of the casing.

According to another characteristic of the invention, the injection device includes a cap with a form adapted so as to close off the front end section of the front part of the casing and to butt up against the rear part of the said causing in the retracted position of the latter.

Such a cap, apart from its conventional protective function, makes it possible to block the front and rear parts of the casing relatively in translation, before use, in the retracted position of the said parts.

In addition, the front part of the casing advantageously incorporates an internal conduit for guiding the syringe body extending over a portion of a length of the-said front part from the front wall of the latter, the said conduit having a shoulder for stopping the said syringe body in its forward position.

The cap also preferably includes claws extending longitudinally inside the said cap and disposed so as to lodge in the inner conduit for guiding the syringe body, the said claws being adapted so as to hook over an end piece protecting the needle of the syringe.

This arrangement makes it possible to withdraw automatically the end piece protecting the needle in a conventional manner, when the cap is removed.

In addition, according to another characteristic of the invention, the rear part of the casing and the cap have contact faces profiled in the shape of a cam so that the said cap can be removed by a rotational movement of the latter.

Figure 6:
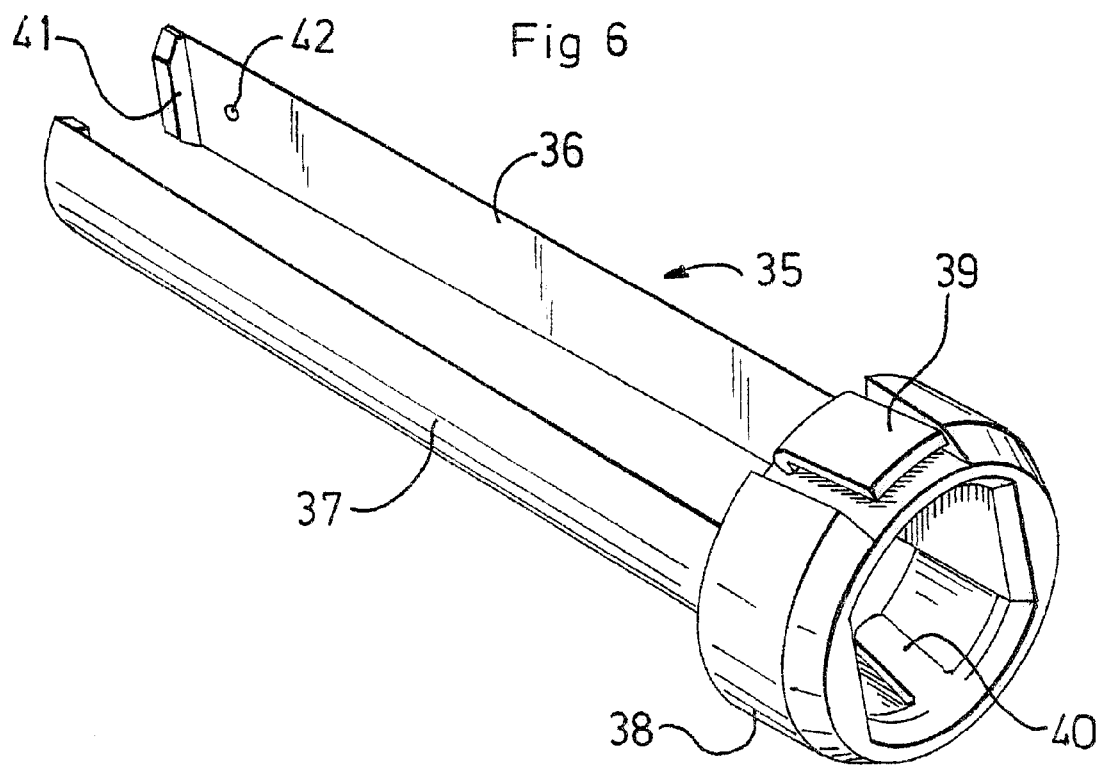
Figure 7:
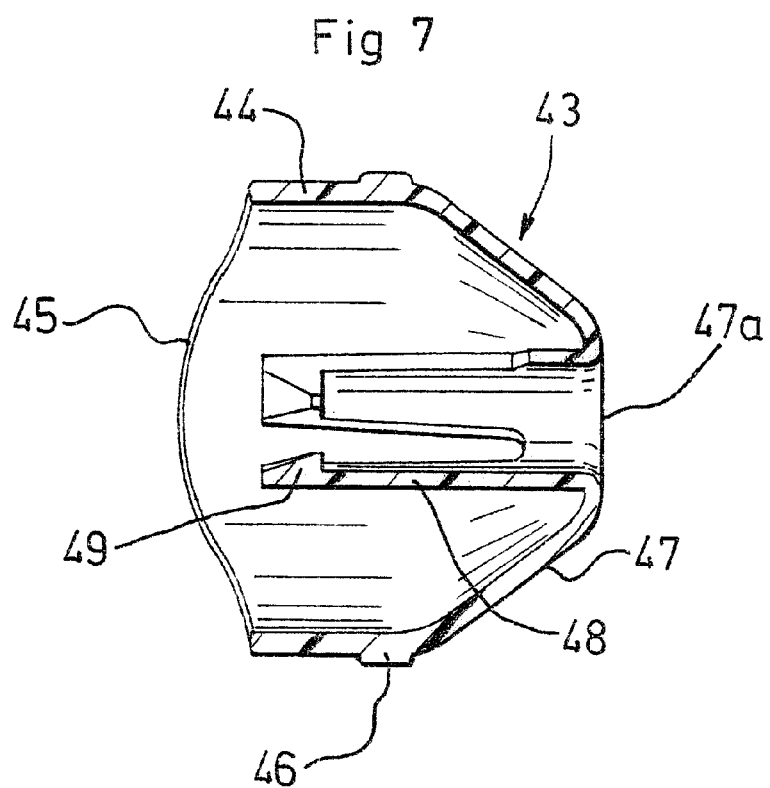
Figure 12:
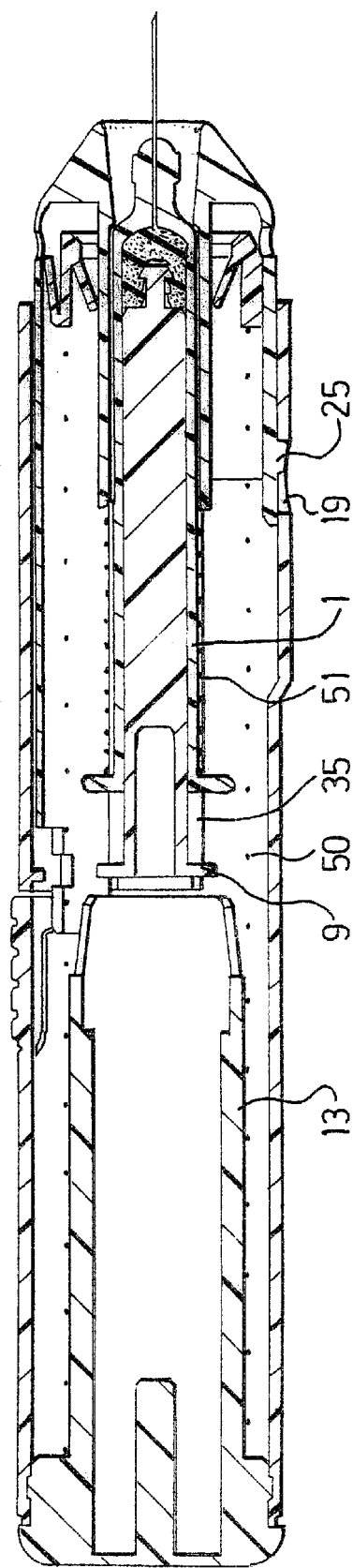
Figure 13:
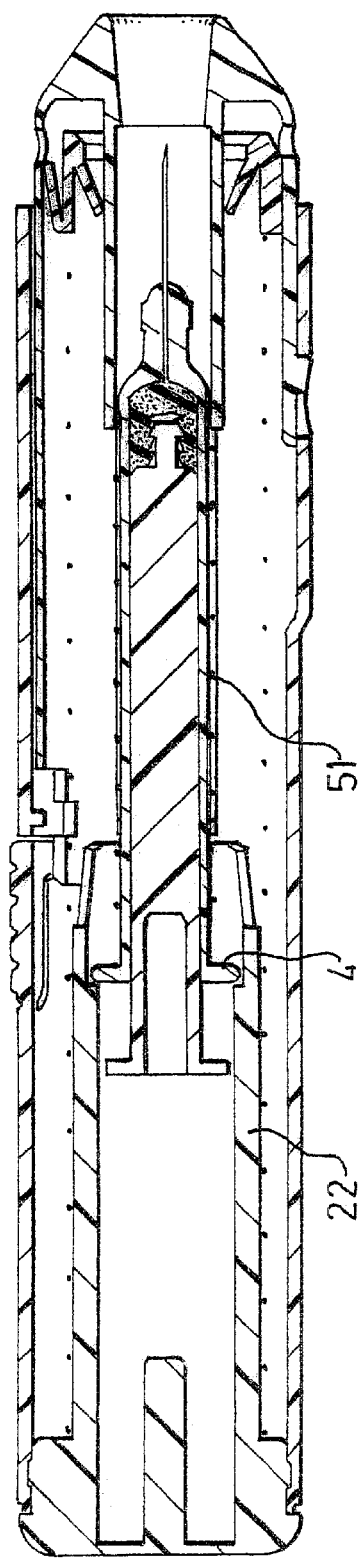
Figure 14:
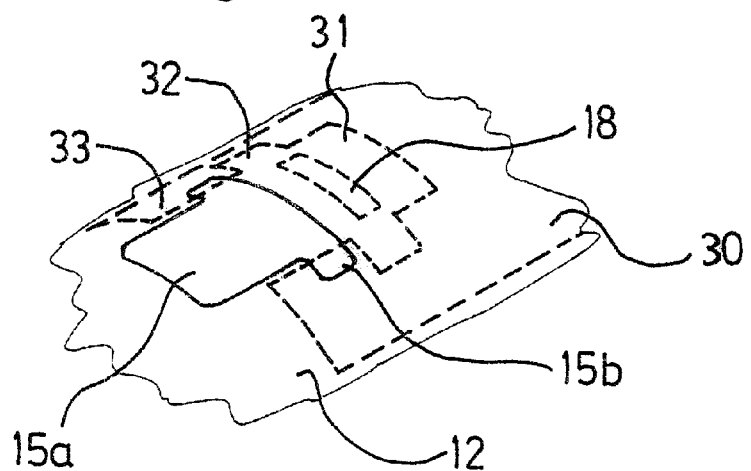
Figure 15:
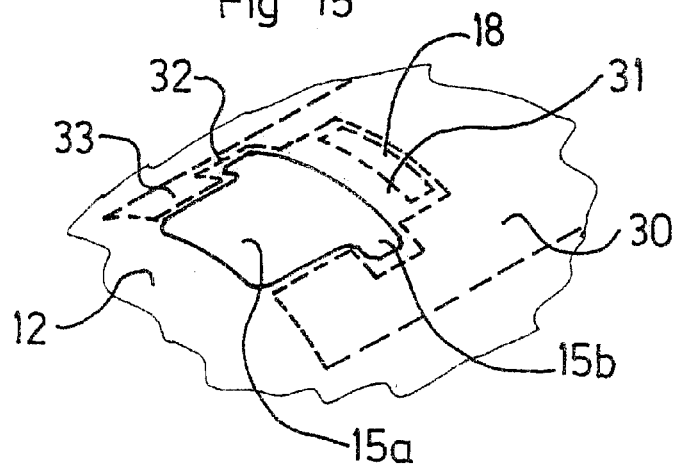
Figure 16:
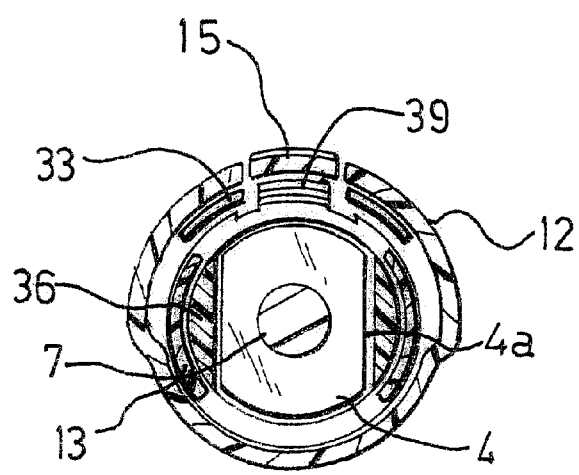

Other characteristics, objects and advantages of the invention will become apparent from the following detailed description with reference to the accompanying drawings which represent, as a non-limiting example, a preferred embodiment thereof. On these drawings, which form an integral part of the present invention:

FIG. 1 is a perspective view of an auto-injection device according to.the invention, FIG. 2 is a longitudinal section through an axial plane of the rear part of the casing of this auto-injection device, FIG. 3 is a longitudinal section through an axial plane B of this rear part of the casing, FIG. 4 is a longitudinal section through the axial plane A of the front part of the casing of this auto-injection device, FIG. 5 is a longitudinal view from above of this front part of the casing, FIG. 6 is a perspective view of the stirrup for supporting the piston rod of the syringe, FIG. 7 is a longitudinal section through the axial plane A of the cap of this auto-injection device, FIGS. 8 to 13 are longitudinal sections through the axial plane A of the auto-injection device according to the invention, illustrating successive steps in the operation of this device, FIGS. 14 and 15 are partial diagrammatic perspective views representing the auto-injection device in the retracted and forward positions respectively of the rear section, the front section of the said auto-injection device being shown in dotted lines, and FIG. 16 is a transverse section through a plane C of this auto-injection device.

The auto-injection device according to the invention, shown in FIGS. 8 to 13, is of the single-use type and is adapted so as to enable the patient to administer to himself or herself a dose of medicinal liquid enclosed in a pre-filled syringe 1 of a traditional type, such as for example one made of glass, and including in a conventional manner:

a neck 2 on which an injection needle 3 is mounted, a rear finger rest ring 4 having a truncated annular form, i.e. possessing, as shown in FIG. 16, two diametrically opposed flats such as 4a, an end piece 5 for protecting the injection needle 3 in the bottom of which the end of the said needle is inserted so as to prevent any outflow of liquid, a stopper 6 acting as a piston, and a piston rod 7 formed over its greater length of a rod 7a with a cruciform cross section extended by a rear tubular section 7b pierced by an axial blind bore 8 emerging in the region of the rear collar 9 with a generally square shape.

This auto-injection device includes, first of all, a casing with a generally cylindrical outer form composed of two parts, a said rear part 10 and a front part 11, one fitted inside the other so as to be able to slide longitudinally one inside the other over a short traverse of the order of a few millimeters.

As shown in FIGS. 2 and 3, the rear part 10 of the casing consists, so that it can be made by injecting a plastic material, of two elements 12, 13 adapted so as to be assembled after manufacture to form an assembly in one piece.

The first of these elements 12 has the form of a sleeve of generally cylindrical form provided with a front end 14 profiled in the form of a cam.

This sleeve 12 is, in addition, provided with a "trigger" delimited by a slot 17 provided in its peripheral wall, and adapted so as to pivot longitudinally and to retract partially inside the said sleeve under the effect of manual pressure.

This trigger 15 has longitudinally the shape of a T of which the longitudinal bar 15a is oriented in the direction of the rear end of the sleeve 12 and has, seen in plan, a rectangular shape adapted so as to be pressed by a finger, so that the transverse bar 15b retracts inside the sleeve 12 when such pressure is applied.

This trigger 15 has, finally, a corrugated upper face provided with transverse ribs such as 16 projecting with respect to the peripheral wall of the sleeve 12.

The sleeve 12 also includes a transverse inner rib 18 in the form of a circular sector, provided opposite the transverse bar 15b of the trigger 15 and separated therefrom by the transverse portion of the slot 17.

This sleeve 12 finally includes an oblong opening 19 with a large longitudinal axis provided in the front quarter section of the said sleeve, in the region of a generating line diametrically opposite the trigger 15.

The second element 13 of the rear section 10 consists of a tube 13 with a generally cylindrical shape, closed in the region of its rear end by an end piece 13a with a shape adapted so as to fit inside the first element 12. This end piece 13a moreover includes a centering pin 20 projecting with respect to its front wall, so as to extend axially into the sleeve 12, over a portion of the length of the latter.

This tube 13 has an external diameter less than the internal diameter of the first element 12 adapted so as to delimit an annular volume 21 inside the latter.

The tube 13 additionally includes internal longitudinal ribs such as 22 distributed around the axis of the tube, extending from the end piece 13a and interrupted at a distance from the front end of the said tube so as to form an axial stop shoulder inside the latter.

This tube 13 finally includes two diametrically opposed cutaways such as 23 which have a trapezoidal shape when seen in plan.

As shown in FIGS. 4 and 5, the front part 11 of the casing includes a cylindrical case 24 with an external diameter adapted so as to be housed inside the rear part 10 of the said casing. In the region of its rear end section, this case 24 is provided with an external pin 25 with a shape adapted so as to be housed inside the oblong opening 19 of the rear part 10. This external pin 25 has moreover a diameter less than the length of the oblong opening 19, adapted so as to allow the front part 11 to slide longitudinally over a short traverse of the order of a few millimeters inside the rear part 10 of the casing.

The case 24 is extended in the region of its front end by a tubular nozzle 26 with a generally frustoconical shape, pierced axially with a frustoconical bore 27b having a cross section which decreases from the end face of the said tubular nozzle.

This frustoconical bore 27b is moreover provided in the extension of a cylindrical conduit 27 for guiding the syringe body, extending axially inside the cylindrical case and separated from the said frustoconical bore by an axial stop shoulder 27c of the said syringe body.

The cylindrical case 24 is moreover pierced next to the tubular nozzle 26 with two diametrically opposed radial openings 28, 29.

The front part 11 of the casing moreover includes a rear longitudinal leg 30 extending into the extension of the cylindrical case 24, and consisting of a portion of the peripheral wall of the said cylindrical case delimiting a circular sector with an angle at the top of the order of 60°.

This longitudinal leg 30 first of all includes an axial opening 31 provided from its rear end, with a width greater than that of the longitudinal bar 15a of the trigger 15 and less than the length of the transverse bar 15b of the said trigger.

This longitudinal leg 30 additionally includes two cut-aways such as 32 arranged facing each other so as to emerge into the opening 31 substantially halfway along the latter and so as to delimit a transverse slot with a length greater than that of the transverse bar 15b of the trigger 15, separated from the rear end of the said longitudinal leg by a region of the wall in the form of a notch 33.

This longitudinal leg 30 finally includes a longitudinal groove 34 provided axially in the extension of the opening 31.

The auto-injection device according to the invention additionally includes a stirrup 35 shown in FIG. 6 for supporting and entraining the piston rod 7 of the syringe 1.

This stirrup 35 first of all has two parallel longitudinal legs 36, 37 separated by a distance and having a cross section adapted so as to be able to slide in the tube 13 of the rear part 10.

This stirrup 35 additionally includes an annular ring 38 made in one piece with the longitudinal legs 36, 37 and inside which are provided the front end sections of the said legs.

Externally, this annular ring 38 has a cutaway with a deformable tongue 39 extending inside it, secured to the said ring in the region of its rear end.

On the inside, this ring 39 has two inclined tongues such as 40, offset by 90° with respect to the longitudinal legs 36, 37 and oriented in the direction of the rear end of the stirrup 35.

Each longitudinal leg 36, 37 of the stirrup 35 additionally includes an internal transverse rib such as 41 provided in the region of the rear end of the said leg and, at a short distance from the said rib, an axial button 42 projecting with respect to the inner face of this leg 36, 37.

The auto-injection device also includes a cap 43 adapted so as to cover the end section of the front part 11 of the casing and including to this end a cylindrical section 44 extended by a frustoconical nozzle 47, with dimensions matching those of the cylindrical case 24 and the tubular nozzle 26.

The rear end 45 of the cylindrical section 44 of this cap 43 has, moreover, the form of a cam matching that of the sleeve 12 of the rear part 10 of the casing, adapted so as to enable the said cap to be removed by a rotational movement imparted to the latter in one or other rotational direction.

The cap 43 also includes external serrations such as 46 provided on the cylindrical section 44 and forming a knurling for manually gripping the said cap.

The cap 43 finally includes an axial front opening 47a provided in the frustoconical nozzle 47 and, extending into this cap 43 from this front opening 47a, three longitudinal claws 48 arranged uniformly around the axis of the said cap.

These claws 48, provided with ends in the form of hooks 49 are provided so as to be retightened when the cap 43 is put in place on the front part 11 of the casing, on account of the frustoconical shape of the bore 27b of the said front part, and so as to hook onto the end piece 45 for protecting the needle 3 of the syringe 1 with a view to enabling the latter to be removed.

The auto-injection device finally includes two propulsion springs 50, 51:

an injection propulsion spring 50 housed in the annular space 21 of the rear part 10 of the casing so as to extend between the front wall of the end piece 13a and the ring 38 of the stirrup 35, a return propulsion spring 51 with a force less than that of the propulsion spring 50, disposed about the syringe 1 so as to extend between the rear end of the cylindrical conduit 27 and the finger rest ring 4 of the said syringe.

The operation of the auto-injection device and the dimensional characteristics of the different constituent elements allowing this.operation are described below with reference to FIGS. 8 to 13.

First of all, as shown in FIG. 8, the initial assembly of the various elements results in:

positioning the syringe 1 relative to the stirrup 35 so that the finger rest ring 4 is positioned butted up against the tongues 40 of the said stirrup, and the collar 9 of the piston rod 7 positioned between the ribs 41 and the buttons 42. In addition, the centering pin 20 then extends into the blind bore 8 of the piston rod 7, positioning the stirrup 35 inside the inner tube 13 so that the tongue 39 of the said stirrup butts up axially against the inner rib 18 of the sleeve 12, while the tongues 40 are housed in the cutaways 23 of the said inner tube.

As emerges from FIG. 8 and according to these arrangements:

the injection propulsion spring 50 is held compressed between the front wall 13a of the tube 13 and the ring 38 of the stirrup 35, the syringe 1 is entirely housed inside the casing, the end of the protective end piece 5 being situated recessed from the end of the nozzle 26, the rear end of the cap 43 and the front end of the rear part 10 of the casing are in contact with each other, so that, on account of the fact that the cap 43 is secured to the front part 11 of the casing, any relative movement is prevented between the front part 11 and the rear part 10 of the casing, the rear part 10 of the casing is situated in a "retracted" position with respect to the front part 11 of the said casing, a position in which, as shown in FIG. 14, the transverse bar 15b of the trigger 15 becomes positioned facing the notches 33, preventing the said trigger from being actuated.

With a view to injection, the first operation consists of withdrawing the cap 43 and simultaneously the end piece 5 protecting the needle 3. This withdrawal is obtained by turning the cap 43 in one direction or another, a rotation during which the cam-shaped profiles 14, 45 lead to the production of an axial movement of the said cap, so that the said withdrawal is similar to a simple unscrewing operation.

Moreover, during this withdrawal, the syringe 1 does not undergo any translational movement on account of the fact that the finger rest ring 4 is butted up against the tongues 40 of the stirrup 35, so that no compression of the return propulsion spring 51 takes place.

The following operation consists of applying the nozzle 26 of the casing against the skin and of exerting a longitudinal pressure on the rear part 10 of the said casing. As shown in FIG. 9, this operation causes the rear part 10 of the casing to move forwards relative to the front part 11, a movement during which relative guiding of the said parts is ensured by the pin 25 housed in the opening 19.

At the end of this relative movement, and as shown in FIGS. 9 and 15, the transverse bar 15b of the trigger 15 is positioned facing the cutaways 32, so that the said trigger can be actuated.

As shown in FIG. 10, injection is then obtained by actuating the trigger 15 which leads to a deformation of the tongue 39 and freeing of the stirrup 35 which, under the effect of the propulsion spring 50:

first of all moves the syringe 1/piston rod 7 assembly until the syringe body butts up against the shoulder 27c of the conduit 27, a movement during which the needle 3 is inserted into the body of the patient (FIG. 10). (In addition, during this movement, the tongue 39 moves in the groove 34, so that the frictional forces of the latter are minimized), then moves the piston rod 7 relative to syringe body 1, resulting in the injection of the product enclosed in the said syringe.

At the end of this injection and as shown in FIG. 11, the ring 38 of the stirrup 35 becomes positioned opposite the openings 28, 29 of the casing so that the patient can see this ring 38 and can therefore be assured of the complete emptying of the syringe 1.

This complete emptying is moreover assured as shown in FIG. 11, on account of the fact that the rear end of the legs 36, 37 of the stirrup 35 still remain positioned inside the inner tube 13 at the end of the traverse of the said stirrup, so that the collar 9 of the piston rod 7 is held pinched between the said legs.

Once the end of the injection has been observed by the patient, the latter has only to release the pressure exerted on the case. This action has the effect of leading to a retraction of the rear part 10 with respect to the front part 11, under the action of the residual force of the injection propulsion spring 50.

As shown in FIG. 12, this retraction results in the freeing of the rear end of the legs 36, 37 of the stirrup 35 which no longer ensure their function of supporting the collar 9 of the piston rod 7.

As shown in FIG. 13, the syringe 1 is then propelled inside the casing under the action of the return propulsion spring 51 until the finger rest ring 4 is butted up against the end of the ribs 22.

The injection device may then be discarded without any risk of subsequent pricking, on account of the fact that, on the one hand, the needle 3 is situated clearly withdrawn from the end of the nozzle 26 of the casing, and on the other hand, that the said device cannot be reactivated.

What is claimed is:

1. A device for automatically injecting a dose of a medicinal product, comprising:
    a long narrow casing having a front wall (26) pierced by an orifice (27b), and formed of two parts, a front part (11) and a rear part (10) fitted one into the other and capable of sliding longitudinally in relation to each other over a short traverse so as to be able to undergo a relative movement between two positions: a retracted rest position, of the rear part (10) with respect to the front part (11) obtained naturally in the absence of an external force exerted on the said parts, and a forward injection position, of the rear part (10) with respect to the front part (11) obtained by means of a longitudinal force exerted on the said rear part,
    a syringe (1) disposed in the casing and including a syringe body housing a piston (6), provided with a finger rest ring (4) and carrying a needle (3),
    a piston rod (7) provided with a collar (9) and extending into the rear extension of the syringe (1),
    means (35) for supporting the collar (9) of the piston rod (7),
    a propulsion spring (50) extending between the means (35) for supporting the collar (9) of the piston rod (7) and the bottom of the rear part (10) of the casing,
    means (15, 18, 39) for locking in translation the means (35) for supporting the collar (9) of the piston rod (7), capable of supporting them inside the casing in a position where the propulsion spring (50) is compressed, and where the syringe (1) is entirely housed inside the said casing, and capable of allowing their movement towards a forward position at the end of injection, produced by the propulsion spring (50), after the parts (10, 11) of the casing are moved from their retracted position to their forward position,
    a device (27c) for stopping the syringe body (1) in a forward position of the latter where the needle (3) extends at least partially through the orifice (27b) of the casing,
    means (13) for triggering the means (35) for supporting the collar (9) of the piston rod (7), capable of freeing the said collar, in the forward position of the said supporting means, after the parts (10, 11) of the casing are moved from their forward position to their retracted position,
    and a return propulsion spring (51) with a force less than that of the propulsion spring (50), disposed around the syringe body (1) so as to be compressed by the finger rest ring (4) of the said syringe body when the latter is moved to its forward position,
    wherein the said injection device:
        includes means for viewing (28, 29) provided in the wall of the casing so as to enable the means (35) for supporting the collar (9) of the piston rod (7) in their forward position to be seen,
        means for supporting the collar (9) of the piston rod (7) comprising:
            an inner guide tube (13) extending into the rear part (10) of the casing so as to delimit a peripheral annular space (21) within the latter adapted so as to house the propulsion spring (50) in the compressed position of the said spring,
            a cage (35) with a form adapted so as to slide inside the guide tube (13), and to house the piston rod (7) and the collar (9) thereof, the said cage including towards one of its ends, the rear end, an internal device (41) for locking the collar (9) of the piston rod (7), capable of deforming radially and, towards its other forward end, a front wall (38) for stopping the propulsion spring (50) and for contacting the means (15, 18, 39) for locking in translation the said supporting means in the retracted position of the latter,
            the said guide tube and cage being adapted so that, in the forward position of the supporting means (35), the device (41) for locking the collar (9) of the piston rod (7) remains imprisoned in the guide tube (13) in the forward relative position of the parts (10, 11) of the casing, and is freed in the retracted relative position of the said parts of the casing.

2. The injection device as claimed in claim 1, wherein the guide tube (13) and the cage (35) have dimensions adapted so as to house the piston rod (7) and the finger rest ring (4) of the syringe body (1), the said cage including an internal device (40) for stopping the finger rest ring (4) of the syringe body (1) in the retracted position of the said cage, and a front wall (38) provided with an opening for permitting relative movement of this cage (35) and the syringe body (1) in the forward position of the latter.

3. The injection device as claimed in claim 2, wherein the finger rest ring (4) of the syringe body (1) has a truncated annular form and includes two diametrically opposed flats (4a), wherein the cage (35) includes a stirrup provided with two longitudinal legs (36, 37) arranged so that each comes into contact with a flat (4a) of the finger rest ring (4).

4. The injection device as claimed in claim 3, wherein the internal device for locking the collar (9) of the piston rod (7) consists of transverse grooves (41) provided facing the legs (36, 37) of the stirrup (35).

5. The injection device as claimed in claim 3, wherein the stirrup (35) includes a ring (38) in the rear extension of which the longitudinal legs (36, 37) extend, the internal device for stopping the finger rest ring (4) of the syringe body (1) including at least one inclined tongue (40) extending longitudinally inside the said ring.

6. The injection device as claimed in claim 1, wherein:

the rear part (10) of the casing has the form externally of a sleeve with a generally cylindrical form, the front part (11) of the casing has dimensions adapted so as to be housed over most of its length inside the rear part (10) of the said casing, guiding devices (19, 25) are adapted so as to enable the rear part (10) of the casing to move over a short traverse along the front part (11) of the said casing.

7. The injection device as claimed in claim 6, wherein the means for locking in translation the means (35) for supporting the collar (9) of the piston rod (7) comprise:

a radially deformable stop device (39) secured to the supporting means (35), an internal axial device (18) for stopping the deformable stop device (39), provided inside the rear part (10) of the casing, a trigger (15) provided in the peripheral wall of the rear part (10) of the casing so that it can deform and free the device (39) for stopping the supporting means (35), in the retracted position of the latter, and an opening (31) provided in the peripheral wall of the front part (11) of the casing and with a form adapted firstly so that the stop devices (18, 39) extend through the said opening and secondly so as to enable the trigger (15) to be actuated only in the forward relative position of the said parts of the casing.

8. The injection device as claimed in claim 7, wherein the trigger (15) has a longitudinal T-shape, the opening (31) having a corresponding shape and being provided so as to have a transverse arm (32) offset longitudinally from the transverse bar (15b) of the trigger (15) in the retracted relative position of the parts (10, 11) of the casing.

9. The injection device as claimed in claim 6, wherein it includes a cap (43) with a form adapted so as to close off the front end section of the front part (11) of the casing and to butt up against the rear part (10) of the said casing in the retracted position of the latter.

10. The injection device as claimed in claim 9, wherein the rear part (10) of the casing and the cap (43) have contact faces (14, 45) profiled in the shape of a cam so that the said cap can be removed by a rotational movement of the latter.

11. The injection device as claimed in claim 1, wherein the front part (11) of the casing incorporates an inner conduit (27) for guiding the syringe body (1) extending over a portion of the length of the said front part from the front wall (26) of the latter, the said conduit having a shoulder (27c) for stopping the said syringe body in its forward position.

12. The injection device as claimed in claim 11, wherein the cap (35) includes claws (48) extending longitudinally inside the said cap and disposed so as to lodge in the inner conduit (27) for guiding the syringe body (1), the said claws being adapted so as to hook over an end piece (5) protecting the needle (3) of the syringe (1).

* * * * *